United States Patent [19]

Westall

[11] 4,234,574
[45] Nov. 18, 1980

[54] SILOXANES

[75] Inventor: Stephen Westall, Barry, Wales

[73] Assignee: Dow Corning Limited, London, England

[21] Appl. No.: 47,192

[22] Filed: Jun. 8, 1979

[30] Foreign Application Priority Data

Jun. 23, 1978 [GB] United Kingdom ............ 27799/78

[51] Int. Cl.$^3$ .................. C07F 7/18; A01N 9/00; A61K 31/695
[52] U.S. Cl. .................... 424/184; 424/DIG. 10; 556/451; 556/452; 556/456
[58] Field of Search ............... 260/448.8 R; 424/184, 424/DIG. 10

[56] References Cited

U.S. PATENT DOCUMENTS

| | | | |
|---|---|---|---|
| 2,559,342 | 7/1951 | Burkhard | 260/448.8 R |
| 3,536,744 | 10/1970 | Dear | 260/448.8 R |
| 3,536,745 | 10/1970 | Dear | 260/448.8 R |
| 3,839,383 | 10/1974 | Kotzsch et al. | 260/448.8 R |

Primary Examiner—Paul F. Shaver
Attorney, Agent, or Firm—Robert F. Fleming, Jr.

[57] ABSTRACT

Siloxanes having units containing the grouping (XOQO) Si≡ in which X represents hydrogen or a chemical bond linking the adjacent oxygen atom to the silicon atom of a silyl or siloxy group and Q represents

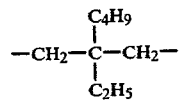

or

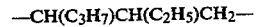

They are prepared by reacting a siloxane with 2-butyl-2-ethylpropane-1,3-diol or 2-ethylhexane-1,3-diol and are useful for imparting insect repellent properties to surfaces.

4 Claims, No Drawings

SILOXANES

This invention relates to siloxanes having silicon-bonded substituents which are derivable from certain alcohols. The invention also relates to a method for the preparation of said siloxanes and to their use for imparting insect-repellent properties to surfaces.

It is known from U.K. Pat. No. 1,232,874 that silanes may be reacted with certain aliphatic diols to provide silicon-containing compounds which are stated to be useful as hydraulic fluids, heat transfer fluids, lubricants, and in some instances, insect repellants. The silane reactants are those of the general formula R'SiX$_3$, wherein X represents a hydrolysable radical, and the products contain heterocyclic structures resulting from the reaction between two of the X groups with both hydroxyl groups in the diol.

According to the present invention there is provided a siloxane having at least one structural unit of the general formula

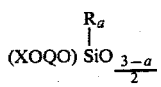  (I)

any remaining units in the siloxane having the general formula

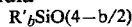  (II)

wherein X represents a hydrogen atom or a chemical bond linking the adjacent oxygen atom to the silicon atom of a silyl or siloxy group (with the proviso that both of the oxygen atoms in the XOQO— group are not attached to the same silicon atom), Q represents the group

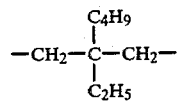

or the group —CH(C$_3$H$_7$)CH(C$_2$H$_5$)CH$_2$— each R and each R' represents a chlorine atom, a hydrogen atom, there being not more than one hydrogen atom attached to any silicon atom, or an organic group other than the group XOQO— which is attached to the silicon atom through a silicon-carbon, silicon-oxygen-carbon or silicon-nitrogen linkage, a has a value of 0, 1 or 2 and b has a value of 0, 1, 2 or 3.

In the general formula defining the siloxanes of this invention X preferably represents a hydrogen atom. It may, however, represent a chemical bond joining the adjacent oxygen atom to a silicon atom of a silyl group or a siloxy group provided that the two oxygen atoms in the XOQO— group are joined to different silicon atoms. Illustrative of such silyl and siloxy groups are those of the general formulae R"$_3$Si—, R"$_3$Si(OSiR"$_2$)$_x$ and R"SiO$_{3/2}$ wherein each R" represents a hydrogen atom, there being not more than one hydrogen atom attached directly to any silicon atom, a chlorine atom, an organic group as defined for R' or an (XOQO)— group, and x is an integer.

Preferably each R and each R' are selected from monovalent hydrocarbon groups and monovalent groups composed of carbon, hydrogen and oxygen for example alkyl, alkenyl, aryl, alkaryl, aralkyl, alkoxy, alkoxyalkoxy and aryloxy. The groups R and R' may, however, also be, for example, monovalent halogenated hydrocarbon groups such as chloropropyl and trifluoropropyl, amino-substituted hydrocarbon groups and quaternary ammonium substituted hydrocarbon groups. Specific examples of R and R' groups therefore are methyl, ethyl, propyl, butyl, 2,4,4- trimethylpentyl, vinyl, phenyl, benzyl, tolyl, methoxy, ethoxy, methoxyethoxy, phenoxy, benzyloxy, —CH$_2$CH$_2$OCH$_2$CH$_3$,

—(CH$_2$)$_3$NH$_2$, —(CH$_2$)$_3$NH(CH$_2$)$_2$NH$_2$ and —(CH$_2$)$_3$N$^+$(CH$_3$)$_2$C$_{18}$H$_{37}$Cl$^-$. Preferably R and R' are each methyl.

The siloxanes of this invention may be homopolymers and copolymers containing only units of Type I, or they may comprise such units and one or more units falling within the general formula II hereinabove. Depending on the proportions and types of units present the siloxanes may vary from freely flowing liquids to resinous solids.

The siloxanes of this invention may be prepared by a process involving the reaction of the appropriate alcohol, that is 2-butyl-2-ethylpropane-1,3-diol or 2-ethylhexane-1, 3-diol, with a siloxane having in the molecule at least one silicon-bonded atom or group reactive with an hydroxyl group in the alcohol. This invention therefore includes a process for the preparation of siloxanes which comprises reacting together (1) a diol which is 2-butyl-2-ethylpropane-1,3-diol or 2-ethylhexane-1,3-diol or both with (2) a siloxane having at least one unit of the general formula

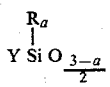

any remaining units in the siloxane having the general formula

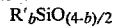

wherein R, R', a and b are as hereinbefore defined and Y represents an atom or group which is reactive with an hydroxyl group in the diol (1).

In the siloxane (2) Y may represent, for example, a hydrogen atom, a chlorine atom, an hydroxyl group, an alkoxy or alkoxy-alkoxy group e.g. methoxy, ethoxy, propoxy, butoxy and methoxy-ethoxy, an amino group e.g. dimethylamino, an acyloxy group or an oximo group. The preferred siloxanes are those in which Y represents a hydrogen atom or an alkoxy or alkoxyalkoxy group having less than 4 carbon atoms.

The siloxanes (2) may vary in nature from resinous polymers to freely flowing liquids in which the ratio of R and R' groups to silicon atoms may vary from below 1.0 to 2.5. Illustrative of the siloxanes (2) which may be employed in the preparation of the siloxanes of this invention are phenylsiloxane resins, methylsiloxane resins, propylsiloxane resins, 2,4,4-trimethylpentylsiloxane resins having silicon-bonded alkoxy groups therein, polymers and copolymers having methylhydrogensiloxane units therein, for example

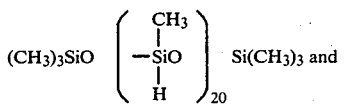

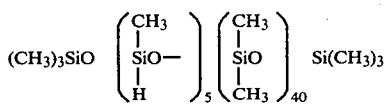

polydiorganosiloxanes having silicon-bonded chlorine atoms or silicon-bonded alkoxy groups therein, for example

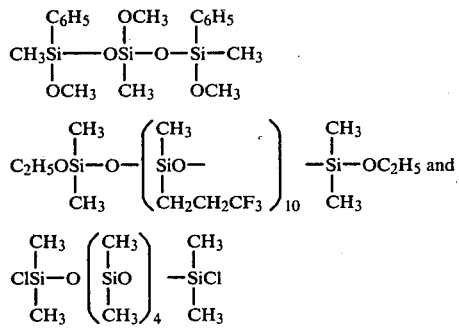

Depending on the nature of the siloxane reactant (2) some reaction between said siloxane and the diol can occur on merely bringing the reactants together at room temperature. It is however, preferred to expedite the reaction by use of the elevated temperatures, preferably from about 40° C. up to the reflux temperature of the reaction mixture. The reaction may also be assisted by the use of a suitable catalyst, for example a metal organic compound such as an organic titanate or an organic tin compound when the reactive (Y) groups in siloxane (2) are alkoxy groups. When the reactive groups in siloxane (2) are chlorine it is advantageous to employ an acid acceptor such as pyridine for the by-produced HCl. In the case where Y is hydrogen suitable catalysts include bases and basic salts such as $K_2CO_3$, $BaCO_3$, NaOH, KOH and $NaOCH_3$, and transition metals e.g. platinum on carbon and palladium on carbon.

If desired organic solvents may be employed to facilitate the reaction and/or to assist in recovery of the reaction product. The relative proportions of the reactants (1) and (2) employed in the process of this invention may vary between very wide limits and depend to some extent on the proportion of (XOQO)— groups desired in the siloxane product. When the products are intended for use as insect repellents as described hereinbelow it is usually preferred that the siloxane product contains a high proportion of the (XOQO)— groups. For other applications, however, it may be desired to react only some of the Y groups in siloxane (2) while retaining the remainder for participation in other reactions, for example crosslinking or adhesion, or to introduce other groups having desirable functions. Depending upon the reaction conditions and reactants employed both of the hydroxyl groups in the diol may be caused to react with Y groups to produce a branched or crosslinked structure. The preferred siloxanes of this invention are, however, those which are soluble in organic solvents, for example hydrocarbons such as toluene, xylene and benzene, and alcohols such as ethanol. Preferably, therefore, the reaction is carried out so as to minimise the formation of highly branched insoluble siloxanes in the product, for example by providing in the reaction mixture an excess of Y groups relative to diol hydroxyl groups.

The siloxanes of this invention undergo hydrolysis in the presence of moisture with the formation of 2-butyl-2-ethylpropane-1,3-diol and/or 2-ethylhexane-1,3- diol which have the property of repelling insects. The diols per se are relatively volatile compounds and are also susceptible to absorption through the skin. Their repellent effect is thus correspondingly short lived. By means of the siloxanes of this invention it is possible to provide relatively nonvolatile compounds which are less susceptible to skin absorption and which release the active ingredient (the diol) over an extended period of time. In many cases such release can be brought about by hydrolysis under the action of, for example, atmospheric moisture or perspiration. The siloxanes therefore find utility as the active constituent in insect repellent compositions or to supplement the action of the conventional active ingredients in such compositions. They may be incorporated into compositions which are intended for application to various surfaces including the human skin, mosquito netting and other barriers normally employed to prevent the access of insects. Such compositions may assume any of the conventional forms, for example creams, sticks and aerosols, wherein the active constituent is normally present in conjunction with one or more diluents or carriers. The insect repellent compositions may therefore contain, in addition the siloxanes of this invention, ingredients such as alcohols e.g. isopropyl alcohol and ethyl alcohol, dimethylpolysiloxanes, perfumes, zinc stearate, magnesium stearate, mineral oil, waxes, lanolin, hydrogenated castor oil, surfactants, propellants and dyes.

When it is desired to increase the rate of hydrolysis of the siloxane (and liberation of the diol) this can be achieved by incorporating a suitable catalyst, for example organic tin compounds and organic titanium compounds such as dibutyltin dilaurate, dibutyltin diacetate, tetraisopropyl titanate and tetra (n-butyl) titanate.

The following examples in which Et=ethyl, Pr=n-propyl and Bu=n-butyl illustrate the invention.

EXAMPLE 1

Dry 2-ethylhexane-1,3-diol(0.73.11 g., 0.50 mol) was charged to a 250 ml. flask equipped with a Dean and Stark apparatus, thermometer, addition funnel, condenser and stirrer. Tetraisopropyl-titanate (0.1 g.) was added to the flask and the contents heated to 140° C. The product (45.0 g., 0.5 mol) obtained by the partial hydrolysis and condensation of methyltrimethoxysilane and having the average unit composition $[CH_3Si(OCH_3)_{0.94}O_{1.06}]$ was then added dropwise to the flask over a period of one hour with stirring. The reaction mixture was maintained at 140° C. for a further one hour until evolution of methanol had ceased; 16 ml. of the methanol being collected.

Vacuum distillation of the resulting reaction mixture removed unreacted diol (21.7 g.) B.p. 130° C., 0.1 mm. Hg) to leave a clear, viscous residue. N.m.r. and i.r. analysis of the residue (74 g.) showed the absence of unreacted methoxy groups and was consistent with a siloxane (Siloxane A) having the average unit composition:

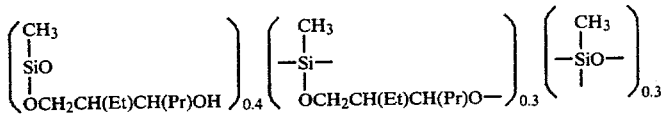

Elemental analysis gave: Found: C, 47.74; H, 8.41; Si, 19.94. Siloxane A requires: C, 47.73: H, 8.91; Si, 19.24.

EXAMPLE 2

2-butyl-2-ethylpropane-1,3-diol (54.4 g., 0.34 mol) dissolved in 150 ml. of dry toluene was charged to a 250 ml. flask equipped with thermometer, reflux condenser and addition funnel. Toluene (50 ml.) was then distilled out to dry the diol azeotropically, potassium carbonate (0.1 g.) added and the contents of the flask heated to 85° C. with stirring. A methylhydrogen polysiloxane (22.02 g., 0.01 mol) of average composition $(CH_3)_3Si[OSi(CH_3)H]_{34}OSi(CH_3)_3$ was dissolved in 50 ml. of toluene and the solution added to the flask dropwise over a period of 45 minutes. Hydrogen was evolved and the reaction mixture was maintained at 80° C. until hydrogen evolution had ceased and i.r. analysis indicated no residual SiH groups.

The reaction misture was cooled and filtered to remove potassium carbonate. Solvent and traces of unreacted diol were removed by vacuum distillation to leave 65.2 g. of a clear viscous residue. N.m.r. and i.r. spectra indicated that the product (Siloxane B) was

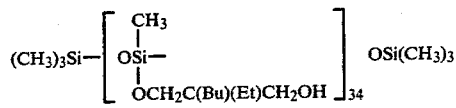

Elemental analysis gave: Found: C, 56.31; H, 10.13; Si, 13.74. Siloxane B requires: C, 54.49; H, 10.24; Si, 13.41.

EXAMPLE 3

2-ethylhexane-1,3-diol (11.70 g., 0.08 mol) and 2-picoline (11.16 g., 0.12 mol) were dissolved in 100 ml. of dry toluene and charged to a 250 ml. flask equipped with stirrer, reflux condenser, thermometer and addition funnel. A chlorine-terminated polydimethylsiloxane having the average composition $ClMe_2Si(OSiMe_2)_{3.25}Cl$ (22.20 g., 0.06 mol) was dissolved in 30 ml. of dry toluene and placed in the addition funnel. The contents of the flask were heated to 50° C. and the chlorosiloxane added dropwise over 45 minutes. After completion of the addition the reaction mixture was refluxed for 3 hours and allowed to cool. 2-picoline hydrochloride (15.4 g.) was then removed by filtration. Toluene was removed from the filtrate by distillation and the residue was vacuum stripped to 110° C. and <1 mm Hg. to leave 23.8 g. of clear, non-viscous liquid. N.m.r. and i.r. analyses were consistent with a siloxane product (Siloxane C) having the average composition:

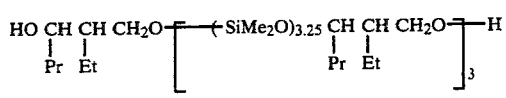

Elemental analysis gave: Found: Si, 47.9%. Siloxane C requires: Si, 48.4%.

EXAMPLE 4

The procedure of Example 3 was repeated using 2-butyl-2-ethylpropane-1,3-diol (12.80 g., 0.08 mol) in place of 2-ethylhexane-1,3-diol. 25.8 G. of a clear, non-viscous fluid was obtained. N.m.r. and i.r. analysis of the product were consistent with a siloxane (Siloxane D) having the average composition:

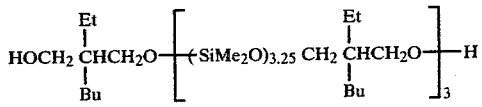

Elemental analysis gave: Found: Si, 46.1%. Siloxane D Requires: Si, 46.7%.

EXAMPLE 5

The performance of the siloxanes as insect repellent substances was examined during a series of trials employing adult Aedes aegypti mosquitos. In one trial nude (Sha-Sha) mice were each treated with 0.4 ml. of a solution in ethanol of 175 mg. of a siloxane having the average unit composition:

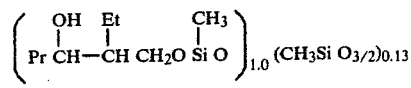

The solution also contained 2% by weight of dibutyltin dilaurate. The quantity (0.4 ml.) of solution was sufficient to treat all of the body surface of each mouse, except the head which was protected throughout the tests. For comparison an equal number of mice were each treated with 0.4 ml. of a solution in ethanol of 100 mg. of 2-ethylhexane-1,3-diol.

Thirty minutes after treatment the mice were placed for 5 minutes in a cage of 30 cm. side containing 200 male and 200 female mosquitos; the cage being maintained at 25° C. and 80–85% relative humidity. The number of mosquitos settling on and biting each mouse was recorded. After 5 minutes the mice were removed from the cage for 30 minutes and then exposed to the mosquitos for a further 5 minutes. This procedure was repeated until the mice were bitten 15 times during a five minute exposure and the total elapsed time recorded as the protection time. Seven such trials were carried out, the same mice being used in all of the trials. It was found that the average protection time for the mice treated with the diol was 70 minutes. For mice treated with the siloxane the average protection time was 90 minutes.

EXAMPLE 6

A trial was conducted using the procedure described in Example 5 except that the human hand was employed as the test subject in place of mice. The hand was covered by a thick rubber glove from the back of which a portion 5 cm.×5 cm. had been cut. The exposed area of the right hand was treated with an ethanol solution of 87.5 mg. of the siloxane used in Example 5 and 2% dibutyltin dilaurate. The exposed area of the left hand was treated with an ethanol solution containing 50 mg. of 2-ethylhexane-1,3-diol.

After 140 minutes had elapsed 10 mosquito bites were recorded on the left hand during a five minute exposure. During the same exposure only 2 bites were recorded on the right hand.

That which is claimed is:

1. A siloxane having at least one structural unit represented by the general formula

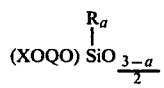  (I)

any remaining units in the siloxane being those represented by the general formula

  (II)

wherein X represents a hydrogen atom or a chemical bond linking the adjacent oxygen atom to the silicon atom of a silyl or siloxy group (with the proviso that both of the oxygen atoms in the XOQO— group are not attached to the same silicon atom), Q represents a group selected from

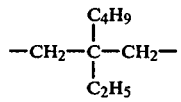

and

each R and each R' represents a chlorine atom, a hydrogen atom, there being not more than one hydrogen atom attached to any silicon atom, or an organic group, other than the group XOQO—, which is attached to the silicon atom through a silicon carbon, silicon-oxygen-carbon or silicon-nitrogen linkage, a has a value of 0, 1 or 2 and b has a value of 0, 1, 2 or 3.

2. A siloxane as claimed in claim 1 wherein X represents a hydrogen atom.

3. An insect repellent composition comprising an effective amount of a siloxane as claimed in claim 1 and one or more diluents or carriers.

4. An insect repellent composition as claimed in claim 3 which also contains a catalyst which accelerates hydrolysis of the siloxane.

* * * * *

UNITED STATES PATENT AND TRADEMARK OFFICE
CERTIFICATE OF CORRECTION

PATENT NO. : 4,234,574
DATED : November 18, 1980
INVENTOR(S) : Stephen Westall

It is certified that error appears in the above-identified patent and that said Letters Patent are hereby corrected as shown below.

In Column 1, line 29; the formula reading "$R'_b SiO_{(4-b/2)}$" should read "$R'_b SiO_{(4-b)/2}$".

Signed and Sealed this

Twenty-second Day of December 1981

[SEAL]

Attest:

Attesting Officer

GERALD J. MOSSINGHOFF

Commissioner of Patents and Trademarks